United States Patent
Tsaur et al.

(10) Patent No.: US 11,654,307 B2
(45) Date of Patent: May 23, 2023

(54) GAS-SUPPLYING MOUTH MASK

(71) Applicant: TO2M CORPORATION, Hsinchu (TW)

(72) Inventors: Garry Tsaur, Rowland Heights, CA (US); Ting-Hua Wang, Rowland Heights, CA (US)

(73) Assignee: TO2M CORPORATION, Hsinchu (TW)

( * ) Notice: Subject to any disclaimer, the term of this patent is extended or adjusted under 35 U.S.C. 154(b) by 413 days.

(21) Appl. No.: 16/877,031

(22) Filed: May 18, 2020

(65) Prior Publication Data
US 2021/0353970 A1 Nov. 18, 2021

(51) Int. Cl.
*A62B 7/08* (2006.01)
*A62B 23/02* (2006.01)
*A62B 18/02* (2006.01)
*A62B 7/10* (2006.01)

(52) U.S. Cl.
CPC .......... *A62B 7/08* (2013.01); *A62B 7/10* (2013.01); *A62B 18/025* (2013.01); *A62B 23/025* (2013.01)

(58) Field of Classification Search
CPC .......... A62B 7/08; A62B 7/10; A62B 18/025; A62B 23/025; A62B 18/003; A61M 16/06; A61M 16/10; A61M 2205/75; A61M 2210/0618
See application file for complete search history.

(56) References Cited

U.S. PATENT DOCUMENTS

2020/0281866 A1\* 9/2020 Tsaur ...................... A61L 15/44

FOREIGN PATENT DOCUMENTS

| CN | 205198649 U | \* | 5/2016 | |
|---|---|---|---|---|
| CN | 108883249 A | \* | 11/2018 | ............ A61M 16/06 |
| CN | 211962827 U | \* | 11/2020 | |
| CN | 212279979 U | \* | 1/2021 | |
| CN | 112295122 A | \* | 2/2021 | |
| JP | 2015217116 A | \* | 12/2015 | |
| JP | 3209283 U | \* | 3/2017 | |
| JP | 2018003197 A | \* | 1/2018 | |
| TW | I648077 | | 8/2016 | |
| TW | M589419 U | | 9/2019 | |

\* cited by examiner

*Primary Examiner* — Tarla R Patel
(74) *Attorney, Agent, or Firm* — Muncy, Geissler, Olds & Lowe, P.C.

(57) ABSTRACT

A gas-supplying mouth mask includes: a mask body for leaning against a user's nose to development of a semi-open space between the mask body and the user's face, wherein the mask body comprising a breathable structure and an airtight structure; and a gas generation unit placed in the mask body for generation of functional gases which can be released to around the user's nose through the breathable structure. Based on the above structures, the gas-supplying mouth mask encircles the functional gases inside the semi-open space formed by the mask body and the user's face and causes a better utilization rate of functional gases.

16 Claims, 6 Drawing Sheets

GAS-SUPPLYING MOUTH MASK

BACKGROUND OF THE INVENTION

1. Field of the Invention

The present disclosure relates to a mouth mask, particularly a multi-functional mouth mask with a better structure.

2. Description of the Prior Art

In recent years, mouth masks have become requisite sanitary products of a family because of all kinds of factors such as haze and public hygiene. For comfort, convenience and functionality of a mouth mask worn on a user, a mouth mask available in the market is characteristic of a distinct structure or diversified functions gradually, for example, a mouth mask covered on a user supplies functional gases.

Taiwan Patent number M583850 discloses a gas permeable layer for supplying hydrogen which can be used in a mask to improve non-bacterial inflammation and other health care effects.

Taiwan patent number I648077 discloses a ventilative mouth mask with oxygen-supplying and dehumidification functions comprises a functional layer for supply of oxygen and dehumidification. The functional layer with functions to lower humidity and generate oxygen is capable of improving air quality inside a mouth mask by supply of oxygen and dehumidification.

However, distinct functional gases supplied by an existing gas-supplying mouth mask worn on a user fail to be inhaled by a mask user and dissipate into outside of a mask due to air permeability of the mask such that utilization rate of functional gases is not high enough. Accordingly, the problem of gas dissipation in a gas-supplying mouth mask deserves to be solved.

SUMMARY OF THE INVENTION

The present disclosure aims to provide a gas-supplying mouth mask (100) for no dissipations but better utilization rate of functional gases, comprising:

a mask body (1) for leaning against a user's nose and forming a semi-open space (2) between the mask body (1) and the user's face, wherein the mask body (1) comprises a breathable structure (11) and an airtight structure (12); and a gas generation unit (3) placed in the mask body (1) for generation of functional gases (5) which are lighter than air; wherein the functional gases (5) can be released to around the user's nose through the breathable structure (11) and encircled by the airtight structure (12) and retained in the semi-open space (2).

To this end, both the breathable structure (11) and the airtight structure (12) form an accommodating interlayer (13) in which the gas generation unit (3) is placed.

To this end, the mask body (1) further has at least one waterproof connector (14) with an opening (141) thereon such that an accommodating space (15) is developed by sealing the side at which the opening of the waterproof connector (14) is located and the breathable structure (11); the gas generation unit (3) is placed in the accommodating space (15).

To this end, the gas-supplying mouth mask (100) further comprises a respiratory region (4) which extends at the downside of the mask body (1), covers a mask user's nasal or oral area and is made of breathable materials for development of a confined space among the respiratory region (4), the mask body (1) and the user's face.

To this end, the respiratory region (4) can be a single-deck or composite-layer component.

To this end, the breathable materials comprise filter media.

To this end, the filter media are selected from a group consisting of nonwoven, cotton material, activated carbon, N95 filter medium and N99 filter medium.

To this end, the breathable materials comprise polymer water-absorbing materials through which perspiration on a user's skin is absorbed.

To this end, the functional gases (5) are hydrogen.

To this end, the gas generation unit is a hydrogen-generation composition, comprising:

(1) Metal hydroxides or metal peroxides and powdered aluminum;

(2) Hydrides; or (3) A combination of above two substances.

To this end, the metal hydroxides comprise calcium hydroxide, magnesium hydroxide, sodium hydroxide or potassium hydroxide.

To this end, the metal peroxides comprise calcium peroxide, magnesium peroxide, sodium peroxide or potassium peroxide.

To this end, the hydrides comprise substances which react with water for generation of hydrogen.

To this end, the weight ratio of the metal peroxides or the metal hydroxides to the powdered aluminum ranges from 1:100 to 100:1.

To this end, the weight ratio of the metal peroxides or the metal hydroxides to the powdered aluminum ranges from 1:10 to 10:1.

To this end, the hydrogen-generation composition further comprises solid acids for adjusting a pH value of the hydrogen-generation composition between 4 and 9.

To this end, the solid acids are selected from a group consisting of solid citric acid, solid lactic acid, solid oxalic acid, solid hydrochloric acid, solid phytic acid, and solid silicic acid.

In the present disclosure, a gas-supplying mouth mask (100) in service features the breathable structure (11) of the mask body (1) leans on a user's nose for forming a semi-open space (2) between the breathable structure (11) and the user's face. The functional gases (5) which have been generated by the gas generation unit (3) are released to around the user's nose through the breathable structure (11). Moreover, the specific gravity of the functional gases (5) cause the functional gases (5) to float over air and the functional gases (5) are then encircled by the airtight structure (12) of the mask body (1) and retained in the semi-open space (2) between the mask body (1) and the user's face.

In the present disclosure, a gas-supplying mouth mask is a solution for no dissipations of functional gases and better utilization rate of functional gases which is unattained in the prior art.

These features and advantages of the present invention will be fully understood and appreciated from the following detailed description of the accompanying Drawings.

DETAILED DESCRIPTION OF THE PREFERRED EMBODIMENT

Figure 1:
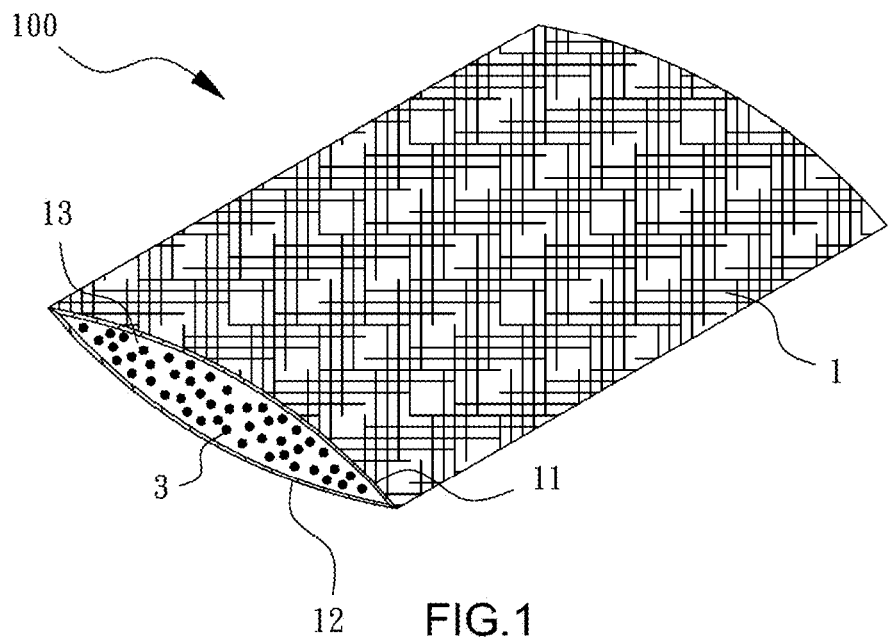
FIG. 1 is a schematic view of a gas-supplying mouth mask in an embodiment.

As shown in FIG. 1 to FIG. 6, a gas-supplying mouth mask (100) in a preferred embodiment of the present disclosure comprises a mask body (1) used to cover a user's nose and a gas generation unit (3) placed in the mask body (1); the mask body (1) and the user's face constitutes a semi-open space (2) and the gas generation unit (3) produces functional gases (5) which are lighter than air.

As shown in the present disclosure, for the functional gases (5) from the gas generation unit (3) available to around the user's nose smoothly, the mask body (1) has a breathable structure (11) through which the functional gases (5) are released into the user's nasal area. For no functional gases (5) dissipated into outside of the gas-supplying mouth mask (100) (that is, the other side opposite to the user's nasal area) through the breathable structure (11), the mask body (1) has an airtight structure (12) with which the functional gases (5) are encircled; wherein the functional gases (5) float over air and retain inside the semi-open space (2) due to blockage of the airtight structure (12).

With manufacturing cost taken into account, the breathable structure (11) as shown in FIG. 1 for a preferred embodiment in the present disclosure links the airtight structure (12) to create a double-deck formation for development of an accommodating interlayer (13) inside; the gas generation unit (3) is placed in the accommodating interlayer (13).

Figure 2:
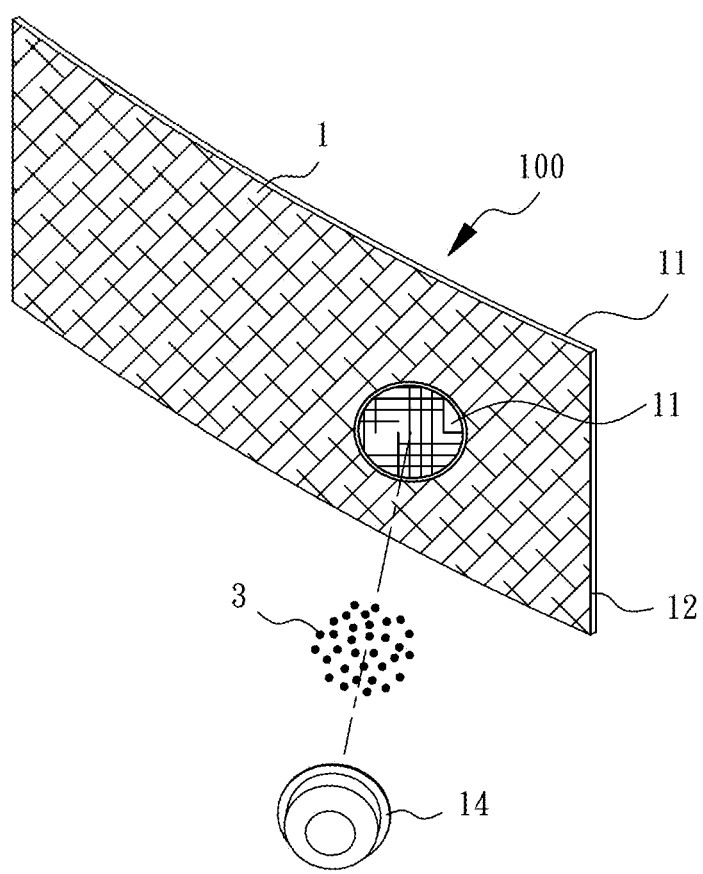
FIG. 2 is an exploded view of a gas-supplying mouth mask in another embodiment.
Figure 3:
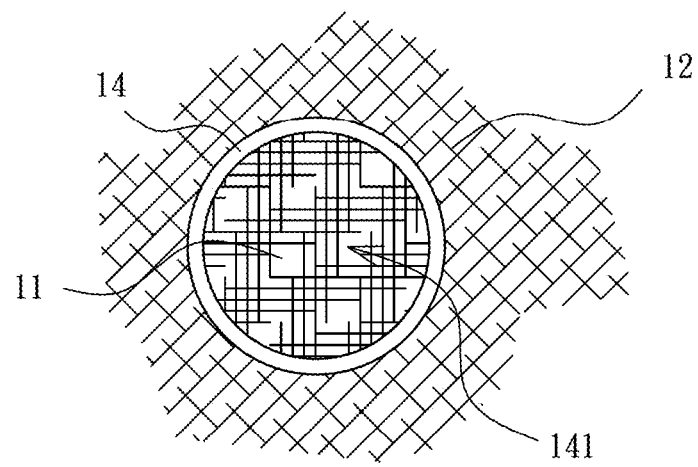
FIG. 3 is a schematic view of a waterproof connector and a breathable structure, both of which are sealed together.
Figure 4:
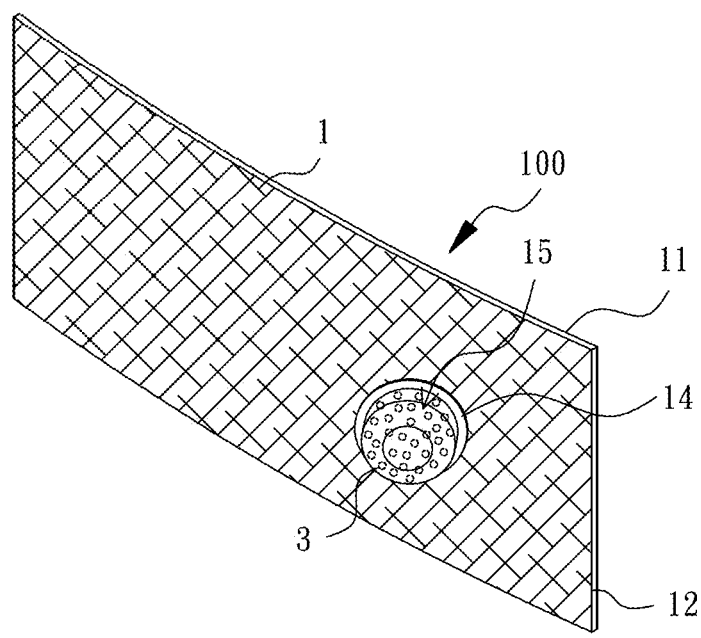
FIG. 4 is a schematic view of a gas-supplying mouth mask in another embodiment.
Figure 5:
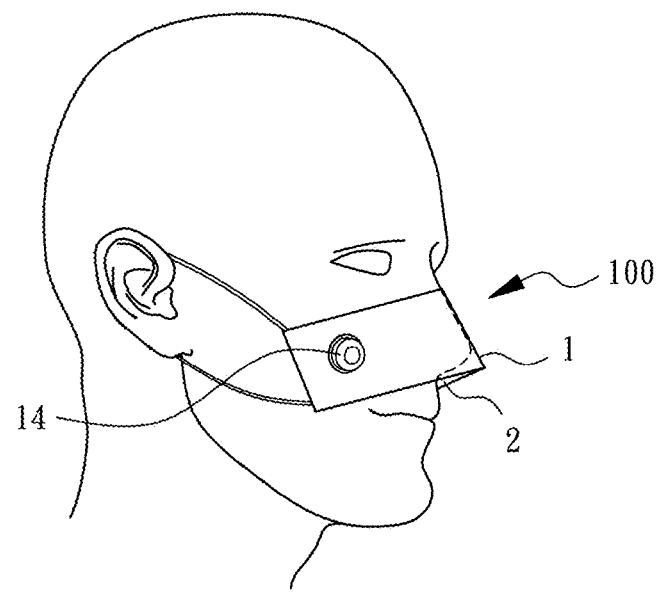
FIG. 5 is a schematic view of a gas-supplying mouth mask in service in another embodiment.
Figure 6:
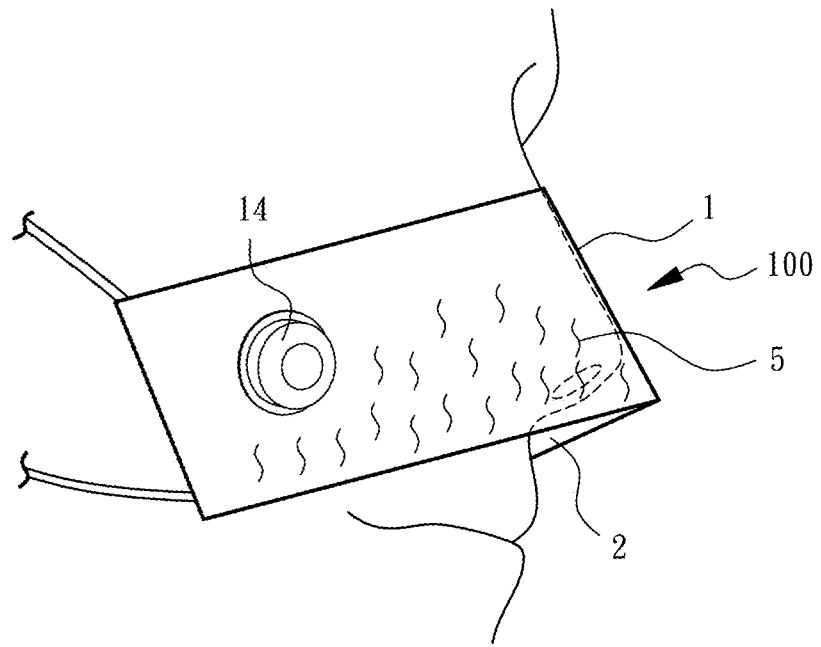
FIG. 6 is a schematic view of a gas-supplying mouth mask in service in another embodiment.

With convenience and comfort of a mask user taken into account, the mask body (1) as shown in FIG. 2 to FIG. 4 for a preferred embodiment in the present disclosure has at least one waterproof connector (14) with an opening (141) thereon such that an accommodating space (15) is developed by sealing the side at which the opening of the waterproof connector (14) is located and the breathable structure (11); the gas generation unit (3) is placed in the accommodating space (15). In the present disclosure, both the breathable structure (11) and the airtight structure (12) are pressed and combined for development of a single-deck planar formation and the breathable structure (11) of the single-deck planar formation features a size limited to the region where the waterproof connector (14) and the breathable structure (11) are sealed together; moreover, both the breathable structure (11) and the airtight structure (12) are connected or pressed and combined for development of a double-deck component in which the airtight structure (12) has a gap such that both the waterproof connector (14) and the breathable structure (11) are sealed through the gap.

Figure 7:
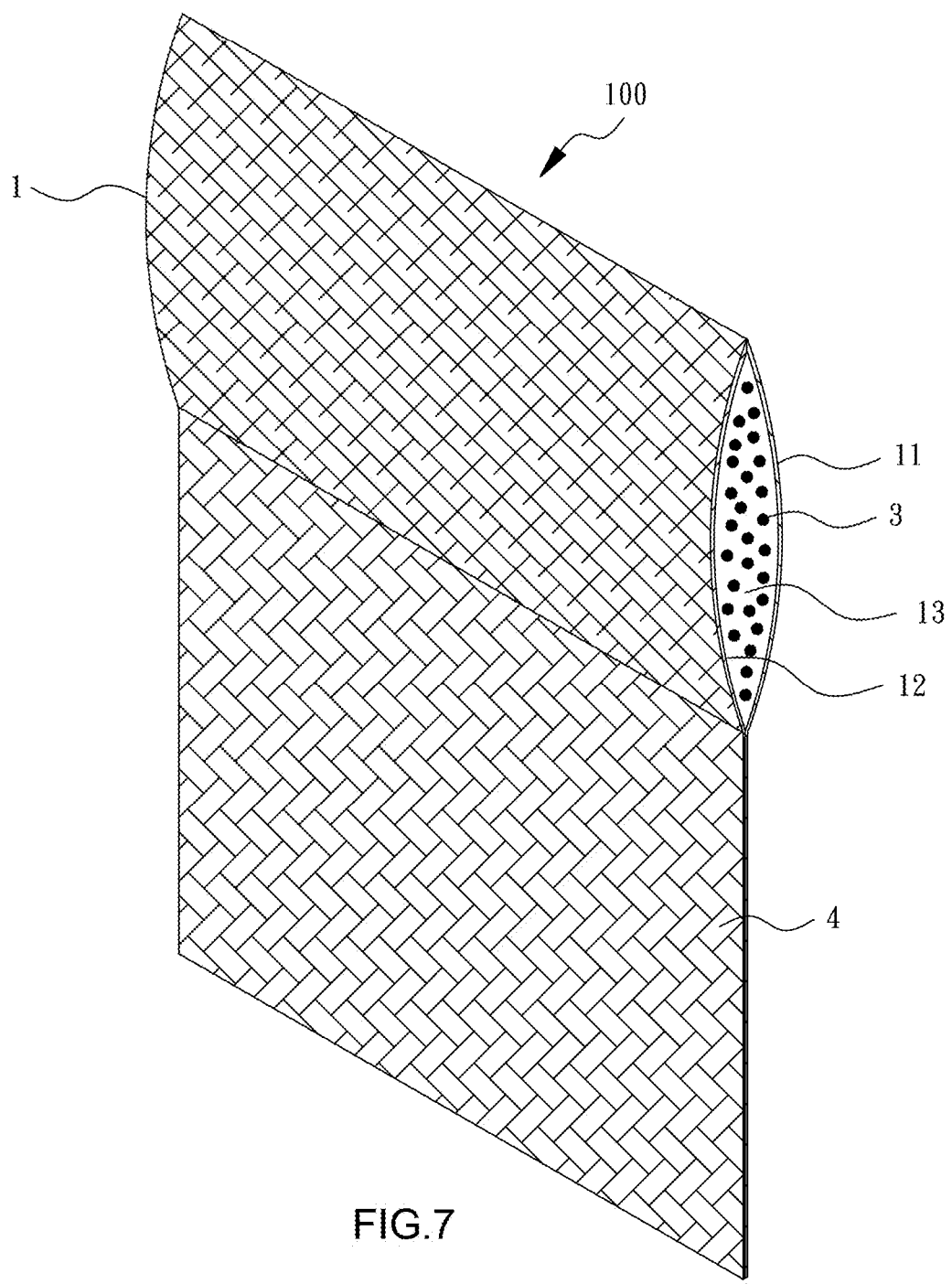
FIG. 7 is a schematic view of a gas-supplying mouth mask in another embodiment.
Figure 8:
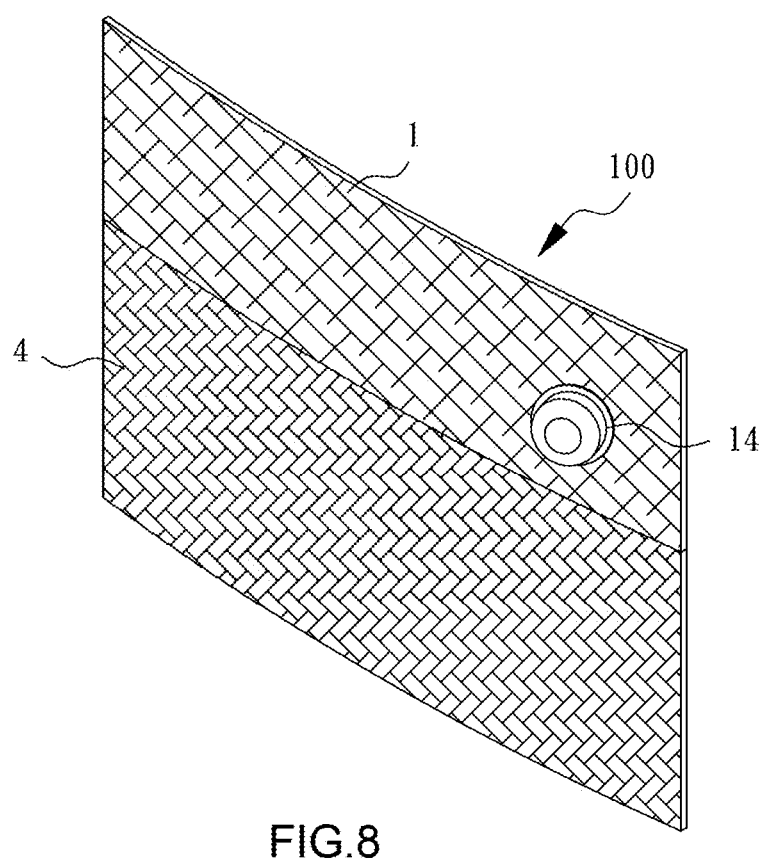
FIG. 8 is a schematic view of a gas-supplying mouth mask in another embodiment.
Figure 9:
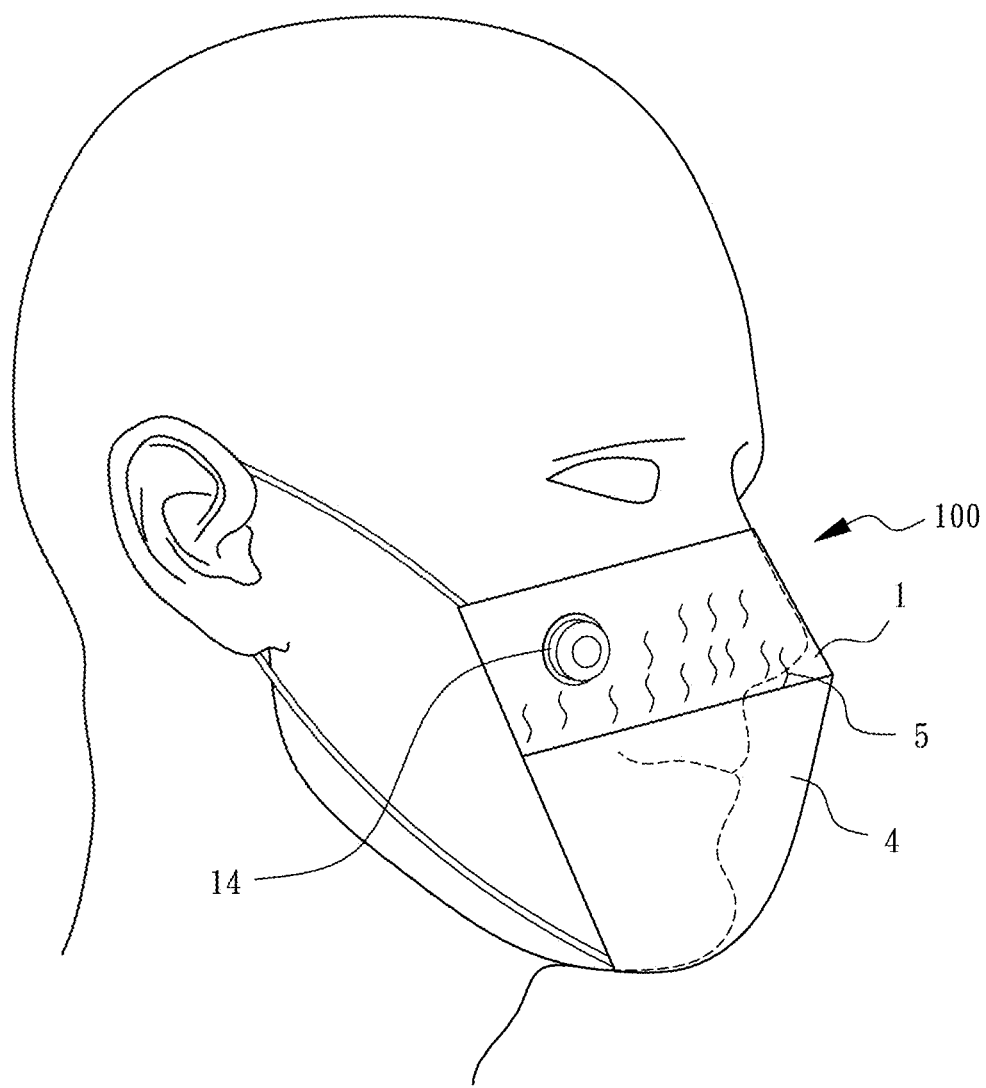
FIG. 9 is a schematic view of a gas-supplying mouth mask in service in another embodiment.

With filterability of a mouth mask taken into account, the gas-supplying mouth mask (100) as shown in FIG. 7 to FIG. 9 for a preferred embodiment in the present disclosure further comprises a respiratory region (4) which extends at the downside of the mask body (1) and covers a user's nasal or oral area for development of a confined space among the respiratory region (4), the mask body (1) and the user's face; the respiratory region (4) made of breathable materials and can be a single-deck or composite-layer component. For good filterability of the gas-supplying mouth mask (100), the breathable materials can be a filter media including, without limitation, nonwoven, cotton material, activated carbon, N95 filter medium or N99 filter medium; for good water absorption of the gas-supplying mouth mask (100), the breathable materials can be made of polymer water-absorbing materials through which perspiration on a user's skin is absorbed.

Embodiment 1: Hydrogen-Supplying Mouth Mask

Hydrogen ($H_2$), a colorless and odorless gas, features its specific gravity of 0.07, that is, 7% of air only, and is so far the lightest gas known to the world. Reportedly, hydrogen has been taken as a biological antioxidant for anti-oxidation, anti-inflammation and anti-apoptosis. Moreover, hydrogen inhaled by a patient can relieve symptoms of neurological or cardiovascular diseases such as stroke and myocardial infarction.

Accordingly, for further supply of hydrogen from the gas-supplying mouth mask (100) in the present disclosure, a hydrogen-generation composition for production of hydrogen is placed in the accommodating interlayer (13) or the accommodating space (15) of the gas-supplying mouth mask (100), as is any other component in previous embodiments, for creation of a hydrogen-supplying mouth mask. For example, the hydrogen-generation composition comprises:

(1) Metal hydroxides or metal peroxides and powdered aluminum;

(2) Hydrides; or (3) A combination of above two substances.

Furthermore, the hydrogen-generation composition is placed in the accommodating interlayer (13) or the accommodating space (15) of the gas-supplying mouth mask (100).

The hydrogen-generation composition can be formed as granules, pastilles or powders. The metal hydroxides comprise calcium hydroxide, magnesium hydroxide, sodium hydroxide or potassium hydroxide. The metal peroxides comprise calcium peroxide, magnesium peroxide, sodium peroxide or potassium peroxide. The hydrides comprise magnesium hydride, calcium hydride or silicon hydride, each of which reacts with water for generation of hydrogen.

When the hydrogen-generation composition comprises metal hydroxides and powdered aluminum, the metal hydroxides react with the powdered aluminum for generation of hydrogen, as shown in Reaction formula 1 or Reaction formula 2.

$$2Al+2H_2O+X(OH)_2 \rightarrow X(AlO_2)_2+3H_2 \text{ (X=calcium or magnesium)} \quad \text{Reaction formula 1:}$$

$$2Al+2H_2O+2Y(OH) \rightarrow 2YAlO_2+3H_2 \text{ (Y=sodium or potassium)} \quad \text{Reaction formula 2:}$$

When the hydrogen-generation composition comprises metal peroxides and powdered aluminum, the metal peroxides react with ambient moistures for generation of metal hydroxides, as shown in Reaction formula 3 or Reaction formula 4, and further generation of hydrogen through the generated metal hydroxides, as shown in Reaction formula 1 or Reaction formula 2.

$$2XO_2+2H_2O \rightarrow 2X(OH)_2+O_2 \text{ (X=calcium or magnesium)} \quad \text{Reaction formula 3:}$$

$$2Y_2O_2+2H_2O \rightarrow 4Y(OH)+O_2 \text{ (Y=sodium or potassium)} \quad \text{Reaction formula 4:}$$

Moreover, for better generation of hydrogen from a hydrogen-supplying mouth mask efficiently, the preferable weight ratio of the metal peroxides or the metal hydroxides in the hydrogen-generation composition to the powdered aluminum ranges from 1:100 to 100:1 and the best weight ratio of the metal peroxides or the metal hydroxides in the hydrogen-generation composition to the powdered aluminum ranges from 1:10 to 10:1.

In addition, for fast generation of much hydrogen from the hydrogen-generation composition, peroxides or hydroxides based on an alkali metal (sodium or potassium) with higher activity can be selected as reactants.

Furthermore, for less skin irritation of a hydrogen-supplying mouth mask and better gas absorption, the hydrogen-generation composition further comprises solid acids to neutralize the above reactions for a pH value between 4 and 9; the solid acids comprise solid citric acid, solid lactic acid, solid oxalic acid, solid hydrochloric acid, solid phytic acid or solid silicic acid.

The above detailed descriptions are feasible embodiments of a gas-supplying mouth mask that should not restrict claims of the present disclosure. Any equivalent application or modification technically without departing from the spirit of the present disclosure, for example, a gas-supplying mouth mask for generation of lighter-than-air functional gases, should be incorporated in claims hereinafter.

In summary, a gas-supplying mouth mask in the present disclosure avoids the problem of functional gases dissipated from a mask in the prior art. To avoid the problem of dissipation and provide better utilization rate of the functional gases, the gas-supplying mouth mask in the present disclosure features an airtight structure, which encircles the functional gases that are lighter than the air and floating over air within the inside of the gas-supplying mouth mask (that is, a side adjacent to a user).

A gas-supplying mouth mask in the present disclosure is characteristic of its structure which makes sure of effects and purposes in service. With a good structure for effects, a gas-supplying mouth mask in the present application meets novelty and non-obviousness for patentability.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A gas-supplying mask, comprising:
a mask body for leaning against a user's nose to form a semi-open space between the mask body and a user's face; wherein the mask body comprises a breathable structure and an airtight structure; and
a gas generation unit placed in the mask body for generation of functional gases which are lighter than air and can be released around the user's nose through the breathable structure and encircled by the airtight structure and retain in the semi-open space; wherein the mask body covering a user's nasal area but not covering a user's oral area wherein the mask body further has at least one waterproof connector with an opening thereon such that an accommodating space is developed by sealing a side at which the opening of the waterproof connector is located and the breathable structure; the gas generation unit is placed in the accommodating space.

2. The gas-supplying mask as claimed in claim 1, wherein both the breathable structure and the airtight structure form an accommodating interlayer in which the gas generation unit is placed.

3. The gas-supplying mask as claimed in claim 1, further comprising a respiratory region which extends at a downside of the mask body for covering the user's nasal area and is made of breathable materials; wherein the respiratory region is able to form a confined space with the mask body and the user's face.

4. The gas-supplying mask as claimed in claim 3, wherein the respiratory region can be a single-deck or a composite-layer component.

5. The gas-supplying mask as claimed in claim 3, wherein the breathable materials comprise filter media.

6. The gas-supplying mask as claimed in claim 5, wherein the filter media are selected from a group consisting of nonwoven, cotton material, activated carbon, N95 filter medium and N99 filter medium.

7. The gas-supplying mask as claimed in claim 3, wherein the breathable materials comprise polymer water-absorbing materials for absorbing perspiration on a user's skin.

8. The gas-supplying mask as claimed in claim 1 wherein the functional gases are hydrogen.

9. The gas-supplying mask as claimed in claim 8, wherein the gas generation unit is a hydrogen-generation composition, comprising:
(1) metal hydroxides or metal peroxides and powdered aluminum;
(2) hydrides; or
(3) A combination of above two substances.

10. The gas-supplying mask as claimed in claim 9, wherein the metal hydroxides comprise calcium hydroxide, magnesium hydroxide, sodium hydroxide or potassium hydroxide.

11. The gas-supplying mask as claimed in claim 9, wherein the metal peroxides comprise calcium peroxide, magnesium peroxide, sodium peroxide or potassium peroxide.

12. The gas-supplying mask as claimed in claim 9, wherein the hydrides comprise substances which react with water for generation of hydrogen.

13. The gas-supplying mask as claimed in claim 9, wherein a weight ratio of the metal peroxides or the metal hydroxides to the powdered aluminum ranges from 1:100 to 100:1.

14. The gas-supplying mask as claimed in claim 9, wherein a weight ratio of the metal peroxides or the metal hydroxides to the powdered aluminum ranges from 1:10 to 10:1.

15. The gas-supplying mask as claimed in claim 9, wherein the hydrogen-generation composition further comprises solid acids for a pH value of the hydrogen-generation composition between 4 and 9.

16. The gas-supplying mask as claimed in claim 15, wherein the solid acids are selected from a group consisting of solid citric acid, solid lactic acid, solid oxalic acid, solid hydrochloric acid, solid phytic acid, and solid silicic acid.

* * * * *